United States Patent
Gregerson et al.

(10) Patent No.: US 6,940,941 B2
(45) Date of Patent: Sep. 6, 2005

(54) BREAKABLE GANTRY APPARATUS FOR MULTIDIMENSIONAL X-RAY BASED IMAGING

(75) Inventors: Eugene A. Gregerson, Bolton, MA (US); Richard K. Grant, Sudbury, MA (US); Norbert Johnson, Methuen, MA (US)

(73) Assignee: Breakaway Imaging, LLC, Littleton, MA (US)

( * ) Notice: Subject to any disclaimer, the term of this patent is extended or adjusted under 35 U.S.C. 154(b) by 16 days.

(21) Appl. No.: 10/319,407

(22) Filed: Dec. 12, 2002

(65) Prior Publication Data

US 2004/0022350 A1 Feb. 5, 2004

Related U.S. Application Data

(60) Provisional application No. 60/357,398, filed on Feb. 15, 2002.

(51) Int. Cl.[7] .................................................. H05G 1/60
(52) U.S. Cl. ........................... 378/4; 378/196; 378/197; 250/363.05
(58) Field of Search ................................ 378/4–20, 193, 378/195–198; 250/363.05, 363.08

(56) References Cited

U.S. PATENT DOCUMENTS

| | | | |
|---|---|---|---|
| 3,549,885 | A | 12/1970 | Anderson |
| 3,617,749 | A | 11/1971 | Massiot |
| 4,200,799 | A | 4/1980 | Saito |
| 4,352,986 | A | 10/1982 | Pfeiler |
| 4,442,489 | A | 4/1984 | Wagner |
| 4,481,656 | A | 11/1984 | Janssen et al. |
| 4,741,015 | A | 4/1988 | Charrier |
| 4,803,714 | A | 2/1989 | Vlasbloem |
| 4,810,881 | A | 3/1989 | Berger et al. |
| 4,829,252 | A | 5/1989 | Kaufman |

(Continued)

FOREIGN PATENT DOCUMENTS

| | | |
|---|---|---|
| DE | 89 05 588.8 | 9/1990 |
| DE | 195 35 583 A1 | 3/1997 |
| DE | 198 39 825 C 1 | 10/1999 |
| DE | 199 27 953 A1 | 1/2001 |
| EP | 0 471 455 A2 | 7/1991 |
| EP | 0 564 292 A2 | 6/1993 |
| EP | 0 810 005 A2 | 12/1997 |
| EP | 1 090 585 A1 | 4/2001 |
| FR | 2 304 321 | 10/1976 |
| GB | 2 088 670 A | 6/1982 |
| WO | WO 96/06561 | 3/1996 |

OTHER PUBLICATIONS

SIREMOBIL Iso–C$^{3D}$ Breathtaking Views in the OR!, SIEMENS, Siemens Aktiengesellschaft Medical Solutions Henkestrasse 127, D–91052 Erlangen, pp. 1–16, no date given.

(Continued)

*Primary Examiner*—Craig E. Church
*Assistant Examiner*—Jurie Yun
(74) *Attorney, Agent, or Firm*—Hamilton, Brook, Smtih & Reynolds, P.C.

(57) ABSTRACT

An x-ray scanning imaging apparatus with a generally O-shaped gantry ring, which has a segment that fully or partially detaches (or "breaks") from the ring to provide an opening through which the object to be imaged may enter interior of the ring in a radial direction. The segment can then be re-attached to enclose the object within the gantry. Once closed, the circular gantry housing remains orbitally fixed and carries an x-ray image-scanning device that can be rotated inside the gantry 360 degrees around the patient either continuously or in a step-wise fashion. The x-ray device is particularly useful for two-dimensional and/or three-dimensional computed tomography (CT) imaging applications.

31 Claims, 11 Drawing Sheets

U.S. PATENT DOCUMENTS

| | | | |
|---|---|---|---|
| 4,875,228 A | 10/1989 | Archer |
| 4,884,293 A | 11/1989 | Koyama |
| 4,935,949 A | 6/1990 | Fujita et al. |
| 4,955,046 A | 9/1990 | Siczek et al. |
| 4,987,585 A | 1/1991 | Kidd et al. |
| 5,014,292 A | 5/1991 | Siczek et al. |
| 5,014,293 A | 5/1991 | Boyd et al. |
| 5,032,990 A | 7/1991 | Eberhard et al. |
| D323,386 S | 1/1992 | Perusek |
| 5,084,908 A | 1/1992 | Alberici et al. |
| 5,095,501 A | 3/1992 | Kobayashi |
| 5,097,497 A | 3/1992 | Deucher et al. |
| 5,159,622 A | 10/1992 | Sakaniwa et al. |
| 5,187,659 A | 2/1993 | Eberhard et al. |
| 5,265,610 A | 11/1993 | Darrow et al. |
| 5,287,274 A | 2/1994 | Saint Felix et al. |
| D345,606 S | 3/1994 | Perusek |
| 5,319,693 A | 6/1994 | Eberhard et al. |
| 5,390,112 A | 2/1995 | Tam |
| 5,448,607 A | 9/1995 | McKenna |
| 5,448,608 A | 9/1995 | Swain et al. |
| 5,452,337 A | 9/1995 | Endo et al. |
| 5,499,415 A | 3/1996 | McKenna |
| 5,515,416 A | 5/1996 | Siczek et al. |
| 5,583,909 A | 12/1996 | Hanover |
| 5,592,523 A | 1/1997 | Tuy et al. |
| 5,625,660 A | 4/1997 | Tuy |
| 5,638,419 A | 6/1997 | Ingwersen |
| 5,661,772 A | 8/1997 | Bär et al. |
| 5,740,222 A | 4/1998 | Fujita et al. |
| 5,740,224 A | 4/1998 | Müller et al. |
| 5,745,545 A | 4/1998 | Hughes |
| 5,784,428 A | 7/1998 | Schmidt |
| 5,802,138 A | 9/1998 | Glasser et al. |
| 5,912,943 A | 6/1999 | Deucher et al. |
| RE36,415 E | 11/1999 | McKenna |
| 6,041,097 A | 3/2000 | Roos et al. |
| 6,147,352 A | 11/2000 | Ashburn |
| 6,203,196 B1 * | 3/2001 | Meyer et al. ............... 378/197 |
| 6,212,251 B1 | 4/2001 | Tomura et al. |
| 6,289,073 B1 | 9/2001 | Sasaki et al. |
| 6,322,251 B1 | 11/2001 | Ballhaus et al. |
| 6,324,246 B1 | 11/2001 | Ruimi |
| 6,325,537 B1 | 12/2001 | Watanabe |
| 6,442,235 B2 | 8/2002 | Koppe et al. |
| 6,484,049 B1 | 11/2002 | Seeley et al. |
| 6,487,267 B1 | 11/2002 | Wolter |
| 6,496,558 B2 | 12/2002 | Graumann |
| 6,609,826 B1 | 8/2003 | Fujii et al. |
| 2003/0072416 A1 | 4/2003 | Rasche et al. |

OTHER PUBLICATIONS

Ning, R., et al., "An Image Intensifier–Based Volume Tomographic Angiography Imaging System", *SPIE* vol. 3032, pp. 238–247.

Chabbal, J., et al., "Amorphous Silicon X–Ray Image Sensor", *Physics of Medical Imaging*, Proceedings of SPIE, Feb. 23–25, 1997, vol. 3032.

Hsiung, H., et al., "3D x–ray angiography: Study of factors affecting projection data consistency", *Physics of Medical Imaging*, Proceedings of SPIE, pp. 226–237, Feb. 23–25, 1997, vol. 3032.

Lwata, K., et al., "Description of a Prototype Combined CT–SPECT System with a Single CdZnTE Detector", *Nuclear Science Symposium Conference Record*, 2000 IEEE, XP010556613, pp. 16–1–16–5.

Lang, T.F., et al., "A Prototype Emission–Transmission Imaging System", *Proceedings of the Nuclear Science Symposium and Medical Imaging Conference*, 1991 IEEE, XP010058199, pp. 1902–1906.

Lang, Thomas, F., et al., "Description of a Prototype Emission—Transmission Computed Tomography Imaging System", *Journal of Nuclear Medicine, Society of Nuclear Medicine*, 1992, XP002901050, pp. 1881–1887.

* cited by examiner

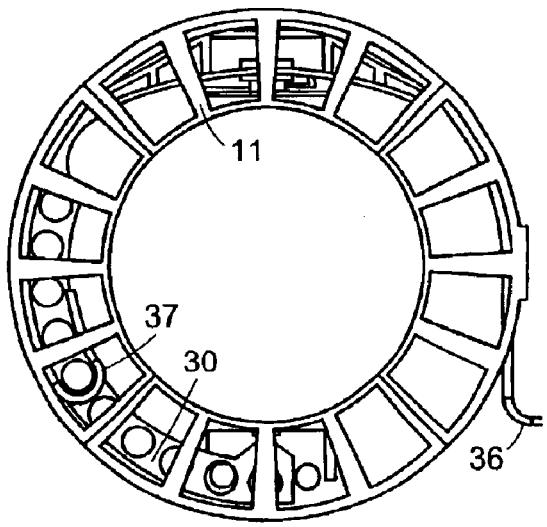
Rotor Angle(0°)
FIG. 15A
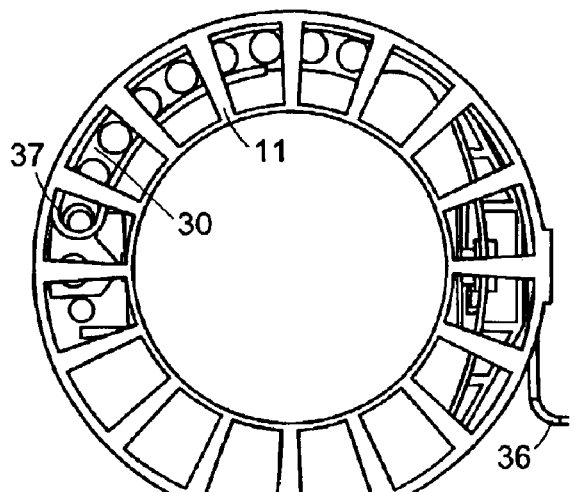
Rotor Angle(90°)
FIG. 15B
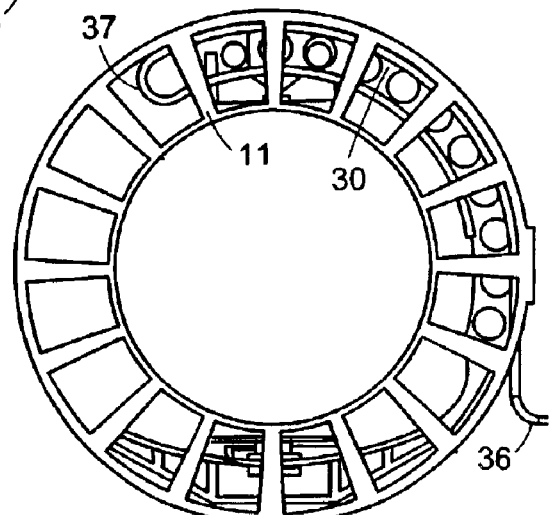
FIG. 15C  Rotor Angle(180°)

Rotor Angle(270°)

Rotor Angle(360°)

BREAKABLE GANTRY APPARATUS FOR MULTIDIMENSIONAL X-RAY BASED IMAGING

RELATED APPLICATION

This application claims the benefit of U.S. Provisional Application No. 60/357,398, filed Feb. 15, 2002, the entire teachings of which are incorporated herein by reference.

BACKGROUND OF THE INVENTION

Healthcare practices have shown the tremendous value of three-dimensional computed tomographic imaging, mainly as a diagnostic tool in the Radiology Department. Other areas of care, including the operating room, intensive care departments and emergency departments, rely on two-dimensional imaging (fluoroscopy, ultrasound, 2-D mobile X-ray) as the primary means of diagnosis and therapeutic guidance. A truly mobile and practical solution for 'non-radiology department' and patient-centric 3-D imaging does not exist. This is mainly due to the fact that current tomographic scanners contain a fixed bore into which the patient must enter from the head or foot. The inability to laterally access a patient and acquire quality images has hindered the acceptance and use of mobile three-dimensional imaging in settings outside of the radiology department.

There is a need for a small scale and/or mobile CT scanner for use in the operating room, procedure rooms, intensive care units, emergency departments and other parts of the hospital, in ambulatory surgery centers, physician offices, and the military battlefield, which can produce high-quality images in a simple and straightforward manner.

SUMMARY OF THE INVENTION

An imaging apparatus comprises a gantry ring having a central opening; a detachable segment of the gantry that provides an opening in the gantry ring through which an object to be imaged may enter and exit the central opening of the ring in a radial direction; a source of radiation within the gantry, the source capable of rotating 360 degrees around the interior of the gantry and which is adapted to project radiation onto an object within the ring; and a detector positioned to detect the projected radiation. In a preferred embodiment, the radiation source is an x-ray source, and the apparatus is used for two-dimensional x-ray or three-dimensional computerized tomographic (CT) imaging.

According to one aspect, the present invention relates to a "detachable" or "breakable" gantry ring, where a segment of the gantry at least partially detaches from the gantry ring to provide an opening or "break" in the ring through which the object to be imaged may enter and exit the central imaging area of the gantry ring in a radial direction. The terms "detachable" and "breakable" as used herein shall have the same meaning as applied to a segment of the gantry ring; that is, the segment can be totally or partially separated from the ring per se, and/or remain attached such as by a hinge, or telescoped around the ring, or via any other means which leaves a radial entrance to the ring interior. In certain embodiments, the segment is secured to the gantry via a hinge, so that the segment swings out like a door. In other embodiments, the segment telescopes with, or piggy-backs on the fixed portion of the gantry. In still other embodiments, the segment is fully detachable and re-attachable from the fixed portion of the gantry.

In certain embodiments, the gantry includes a source of electromagnetic radiation and detector disposed opposite one another on the gantry. The source and detector can be secured to a motorized rotor, which rotates the source and detector around the interior of the gantry in coordination with one another. The gantry can further include a rail and bearing system for guiding the rotor as it rotates, carrying the source and detector.

The invention also relates to a method for imaging an object comprising positioning the object within a gantry ring via a radial opening in the gantry ring; and rotating at least one of a radiation source and a radiation detector around the interior of the gantry ring to image the object. In one embodiment, the method comprises at least partially detaching a segment of the gantry to provide a radial opening in the gantry ring, positioning the object within the ring via the radial opening (by moving the object toward the gantry, or by moving gantry toward the object, or both); reattaching the segment to the gantry ring to enclose the object within the ring; and rotating at least one of a radiation source and a radiation detector around the interior of the gantry ring. The source can project radiation into the ring interior, through the object to be imaged, and onto the detector. Preferably, the source is an x-ray source, and the detected x-ray radiation can be used to produce two-dimensional x-ray or three-dimensional computerized tomographic (CT) object images.

An advantage of the present invention relative to conventional CT scanning devices is the ability to manipulate the x-ray gantry around the object to be scanned, and then close the gantry to perform x-ray imaging. For instance, during a medical procedure, a mobile x-ray gantry device of the present invention can easily approach a patient (or be approached by a patient) from a lateral direction, enclose around the patient, and acquire high-quality images (such as three-dimensional x-ray CT images) with minimal disruption of the medical procedure (e.g. to anesthesia, patient monitoring, sterilization, scrub nurses, etc.). In contrast to larger, fixed-bore devices commonly used in hospital radiology departments, the apparatus of the present invention can advantageously be employed in numerous environments, such as operating rooms, procedure rooms, intensive care units, emergency departments and other parts of the hospital, in ambulatory surgery centers, physician offices, and the military battlefield.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 15A–E illustrate an x-ray imaging apparatus having a cable management system for rotating an x-ray source and detector array 360° around the gantry ring.

DETAILED DESCRIPTION OF THE INVENTION

A description of preferred embodiments of the invention follows.

Figure 1:
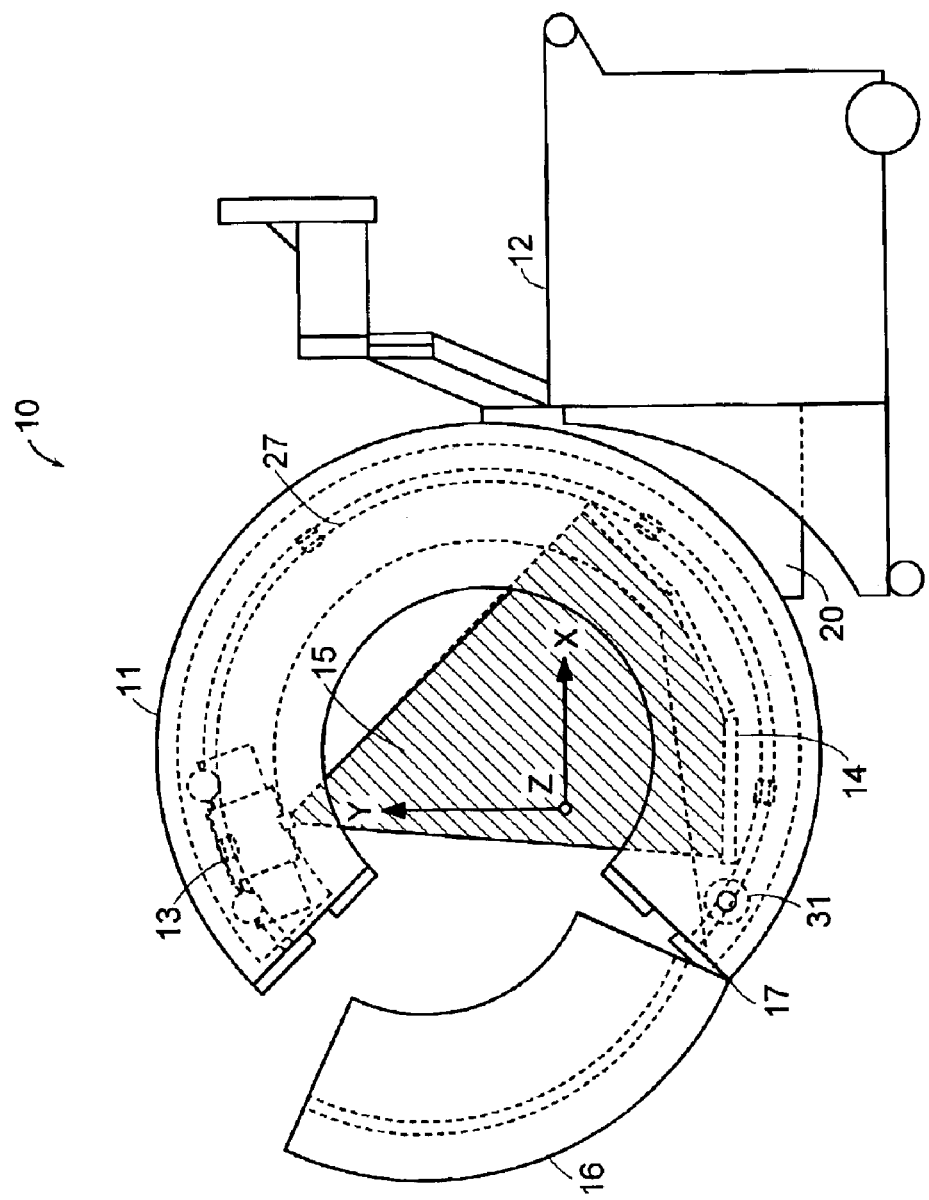
FIG. 1 is a schematic diagram showing an x-ray scanning system with a partially open gantry ring according to one embodiment of the invention.

FIG. 1 is a schematic diagram showing an x-ray scanning system 10, such as a computerized tomographic (CT) x-ray scanner, in accordance with one embodiment of the invention. The x-ray scanning system 10 generally includes a gantry 11 secured to a support structure, which could be a mobile or stationary cart, a patient table, a wall, a floor, or a ceiling. As shown in FIG. 1, the gantry 11 is secured to a mobile cart 12 in a cantilevered fashion via a ring positioning unit 20. In certain embodiments, the ring positioning unit 20 enables the gantry 11 to translate and/or rotate with respect to the support structure, including, for example, translational movement along at least one of the x-, y-, and z-axes, and/or rotation around at least one of the x- and y-axes. X-ray scanning devices with a cantilevered, multiple-degree-of-freedom movable gantry are described in commonly owned U.S. Provisional Applications 60/388,063, filed Jun. 11, 2002, and 60/405,098, filed Aug. 21, 2002, the entire teachings of which are incorporated herein by reference.

The mobile cart 12 of FIG. 1 can optionally include a power supply, an x-ray power generator, a computer system for controlling operation of the x-ray scanning device and for performing image processing, tomographic reconstruction, or other data processing functions, and a display system, which can include a user interface for controlling the device. It will be understood that one or more fixed units can also perform these functions.

The gantry 11 is a generally circular, or "O-shaped," housing having a central opening into which an object being imaged is placed. The gantry 11 contains an x-ray source 13 (such as a rotating anode pulsed x-ray source) that projects a beam of x-ray radiation 15 into the central opening of the gantry, through the object being imaged, and onto a detector array 14 located on the opposite side of the gantry. The x-ray source 13 is also able to rotate 360 degrees around the interior of the gantry 11 in a continuous or step-wise manner so that the x-ray beam can be projected through the object at various angles. At each projection angle, the x-ray radiation beam passes through and is attenuated by the object. The attenuated radiation is then detected by a detector array opposite the x-ray source. Preferably, the gantry includes a detector array that is rotated around the interior of the gantry in coordination with the rotation of the x-ray source so that, for each projection angle, the detector array is positioned opposite the x-ray source on the gantry. The detected x-ray radiation from each of the projection angles can then be processed, using well-known reconstruction techniques, to produce a two-dimensional or three-dimensional object reconstruction image.

In a conventional CT x-ray scanning system, the object being imaged (typically a patient) must enter the imaging area lengthwise from either the front or rear of the gantry (i.e. along the central axis of the gantry opening). This makes it difficult, if not impossible, to employ CT x-ray scanning during many medical procedures, such as surgery, despite the fact that this is where CT scanning applications may be most useful. Also, the conventional CT x-ray scanner is a relatively large, stationary device having a fixed bore, and is typically located in a dedicated x-ray room, such as in the radiology department of a hospital. CT scanning devices are generally not used in a number of environments, such as emergency departments, operating rooms, intensive care units, procedure rooms, ambulatory surgery centers, physician offices, and on the military battlefield. To date, there is not a small-scale or mobile CT scanning device, capable of producing high-quality images at relatively low cost, which can be easily used in various settings and environments, including during medical procedures.

In one aspect, the present invention relates to an improvement on the conventional design of an x-ray imaging device which overcomes these and other deficiencies. In particular, as shown in FIG. 1, the O-shaped gantry 11 includes a segment 16 that at least partially detaches from the gantry ring to provide an opening or "break" in the gantry ring through which the object to be imaged may enter and exit the central imaging area of the gantry ring in a radial direction. In FIG. 1, for instance, a segment 16 of the gantry 11 is secured to the gantry via a hinge 17 which allows the segment to swing out like a door from a fully closed position (see FIG. 2B) to a fully open position (see FIG. 2A). The object being imaged (for instance, a patient) can then enter the gantry from the open side (as opposed to from the front or rear side of the gantry, as in conventional systems), and the hinged segment can then be reattached to fully enclose the object within the gantry ring. (Alternatively, or in addition, the gantry in the open position can be moved towards the object in a lateral direction to position the object within the imaging area, and then the open segment can close around the object.)

Figure 2A:
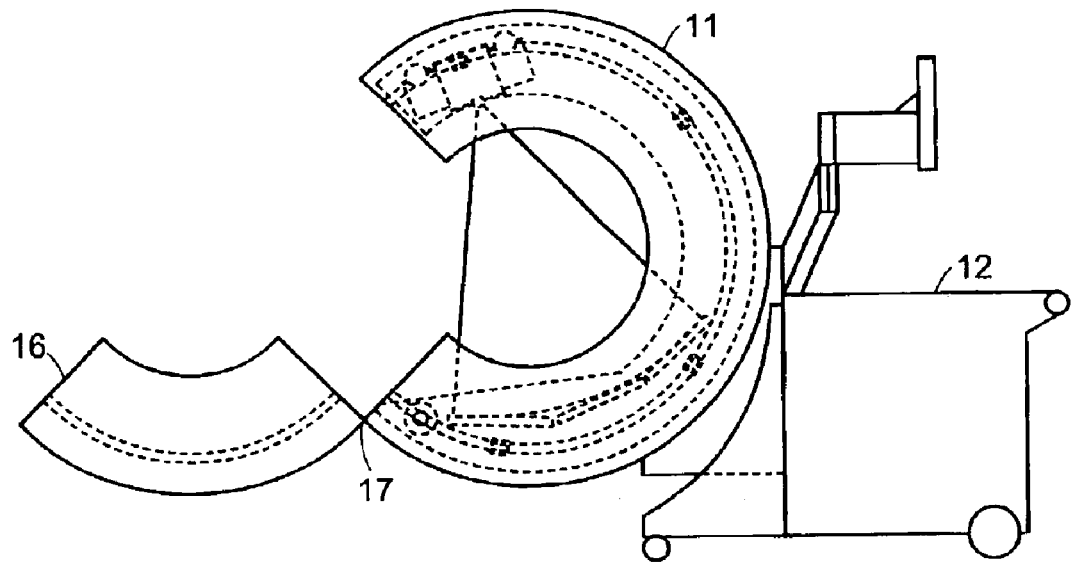
FIGS. 2A and 2B show two side views of the x-ray scanning system of FIG. 1 with a hinged gantry segment in fully open and fully closed positions.
Figure 2B:
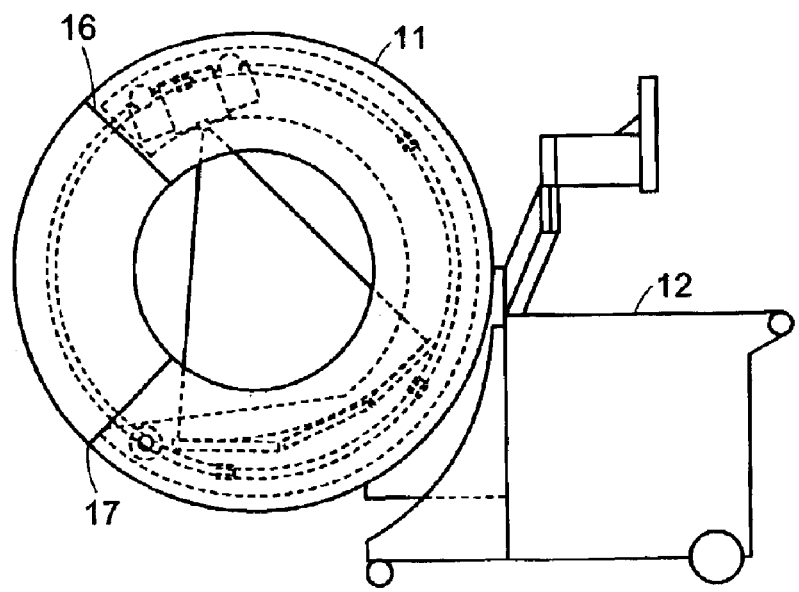

In addition to the hinged door embodiment of FIGS. 1, 2A, and 2B, various other embodiments of the of the gantry assembly are shown in FIGS. 3–7. In each of these systems, a segment of the gantry at least partially detaches from the gantry ring to provide an opening or "break" in the gantry ring through which the object to be imaged may enter and exit the central imaging area of the gantry ring in a radial direction, and wherein the segment can then be reconnected to the gantry to perform 2D x-ray or 3D tomographic x-ray imaging.

Figure 3:
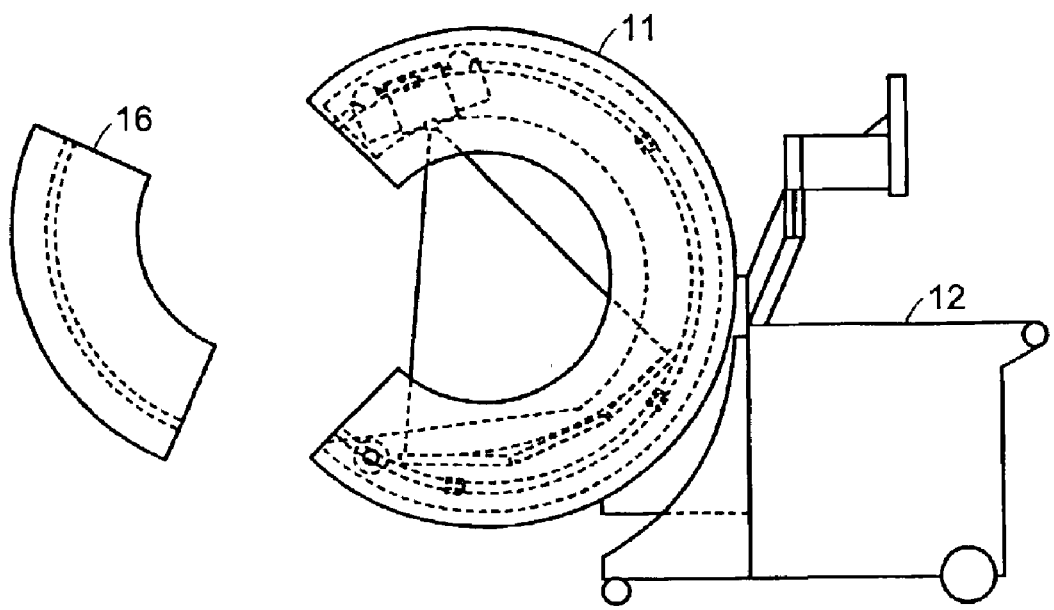
FIG. 3 shows an x-ray scanning system with a detachable gantry segment.
Figure 4:
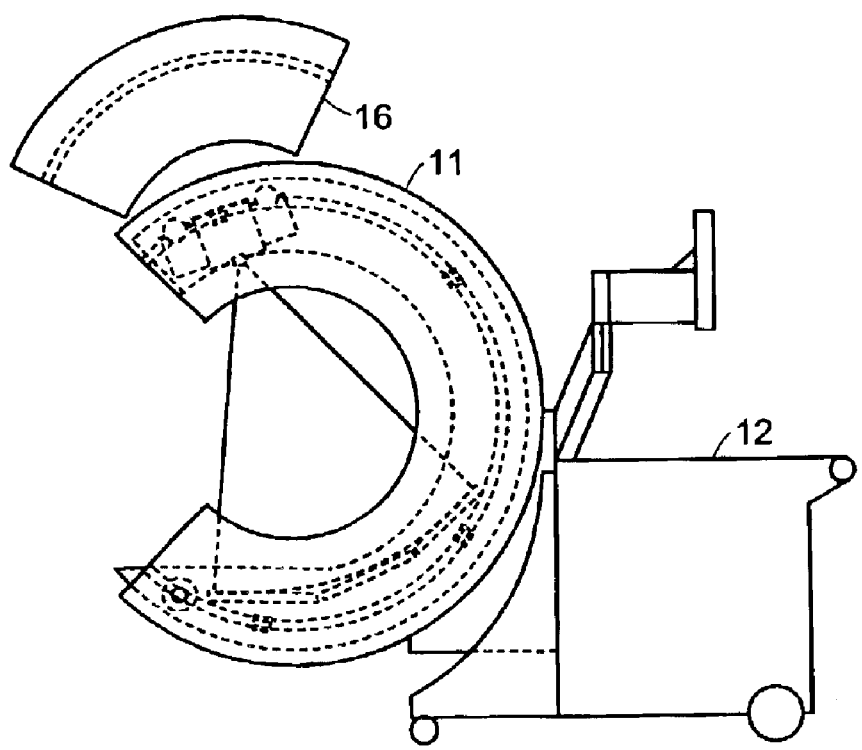
FIG. 4 shows an x-ray scanning system with a piggy back gantry segment.

In FIG. 3, for example, a gantry segment 16 is fully detachable from the fixed portion of the gantry ring 11, and can then be reattached to perform an x-ray imaging process. Similarly, in FIG. 4, the gantry segment 16 fully detaches from the ring to form an opening. In this case, however, the detached segment "piggy backs" on the gantry. This embodiment may include a linkage apparatus which allows the door 16 to detach away from the ring 11 and, while maintaining attached to the ring via the linkage apparatus, swing upwards and circumferentially onto the top of the fixed portion of the gantry ring 11.

Figure 5:
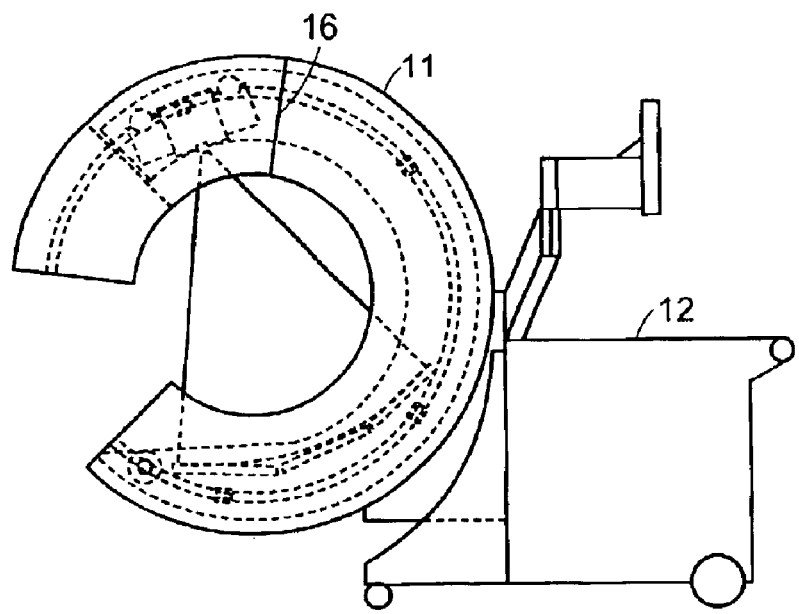
FIG. 5 shows an x-ray scanning system with a telescoping gantry segment.

FIG. 5 illustrates yet another embodiment, where the gantry opens by telescoping the detachable segment 16 with the fixed gantry ring 11. In one embodiment, a the detachable segment 16 can be attached to the gantry ring 11 with alignment pins. A release mechanism releases the pins, and the sidewalls of the segment 16 translate outward relative to the gantry ring, thus allowing the segment 16 to telescope over the fixed upper portion of the gantry ring 11.

Figure 6:
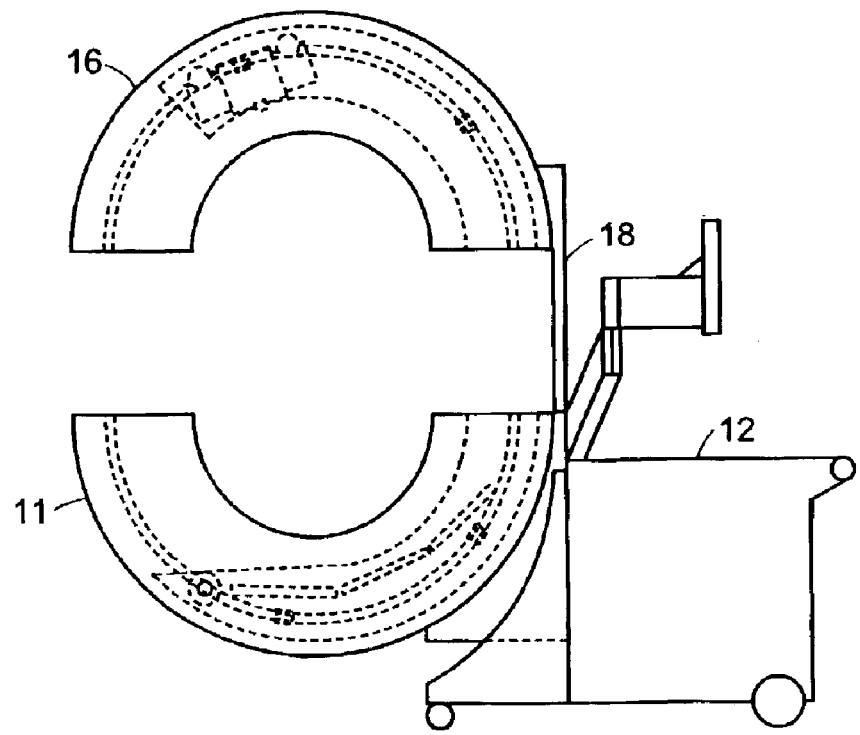
FIG. 6 shows an x-ray scanning system with a vertical lift gantry segment.

In FIG. 6, the gantry opens by lifting a top segment 16 of the gantry off the ring, preferably via a vertical lift mechanism 18 which can be located on the cart 12.

Figure 7:
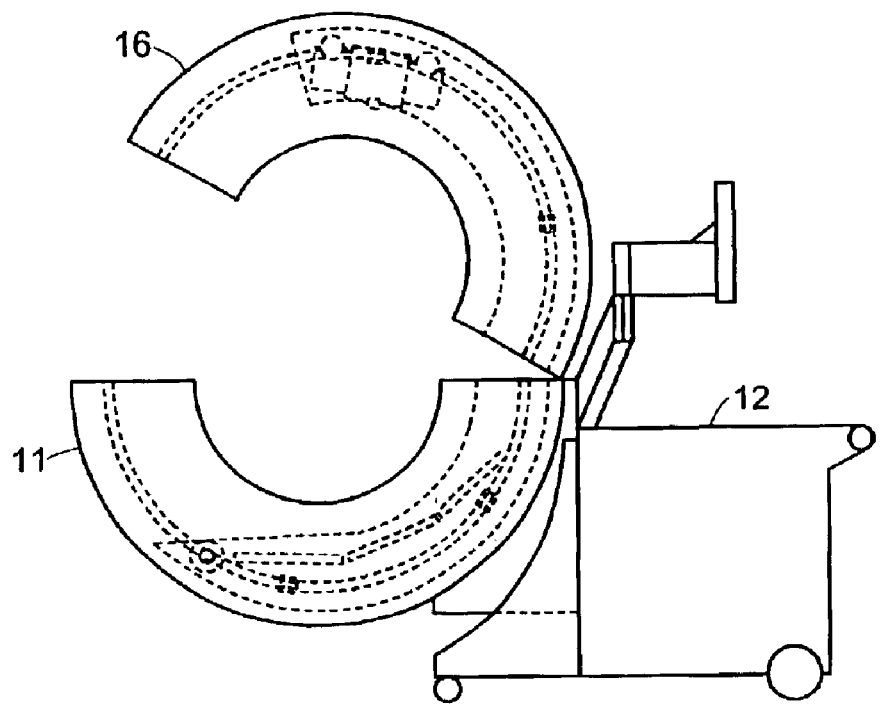
FIG. 7 shows an x-ray scanning system with a pivoted gantry segment.

FIG. 7 shows yet another embodiment with a pivoted gantry segment 16. This is similar to the hinged design of FIG. 1, except here the detachable segment is hinged to the gantry at the side of the gantry opposite the opening, so that the entire top half of the gantry lifts up to access the interior imaging area.

In any of these embodiments, the detachable gantry segment preferably includes a mechanism for securing the segment in place in a closed gantry configuration, yet also permits the segment to be easily detached to open or "break" the gantry ring.

Figure 8:
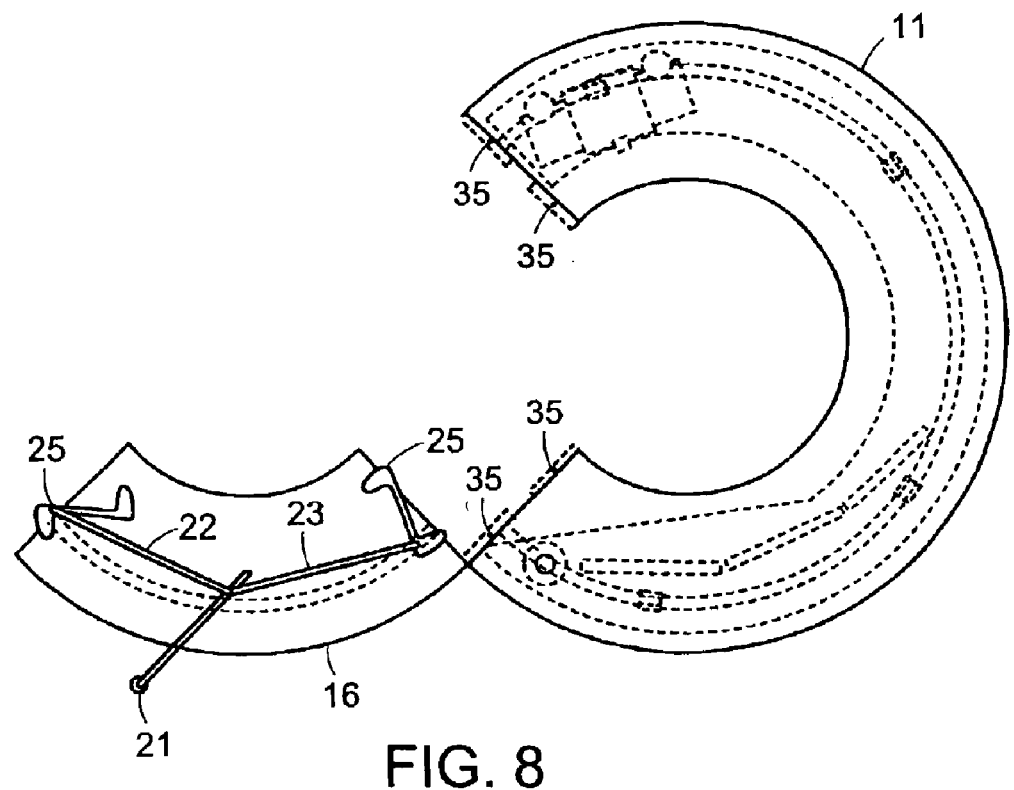
FIG. 8 illustrates a gantry ring for an x-ray scanner system with a hinged gantry segment and a latching mechanism in an open and unlocked position.
Figure 9:
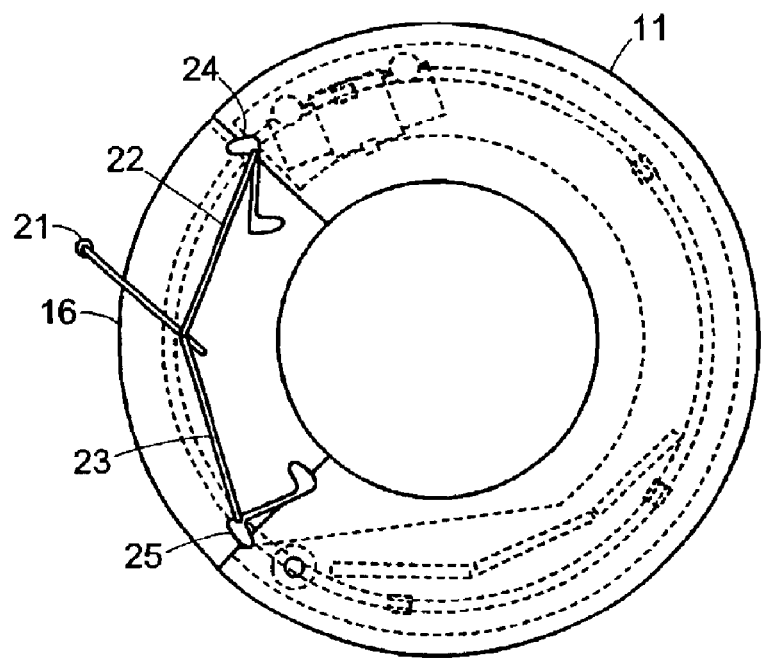
FIG. 9 shows the gantry ring of FIG. 8 with the gantry segment and latching mechanism and a closed and unlocked position.
Figure 10:
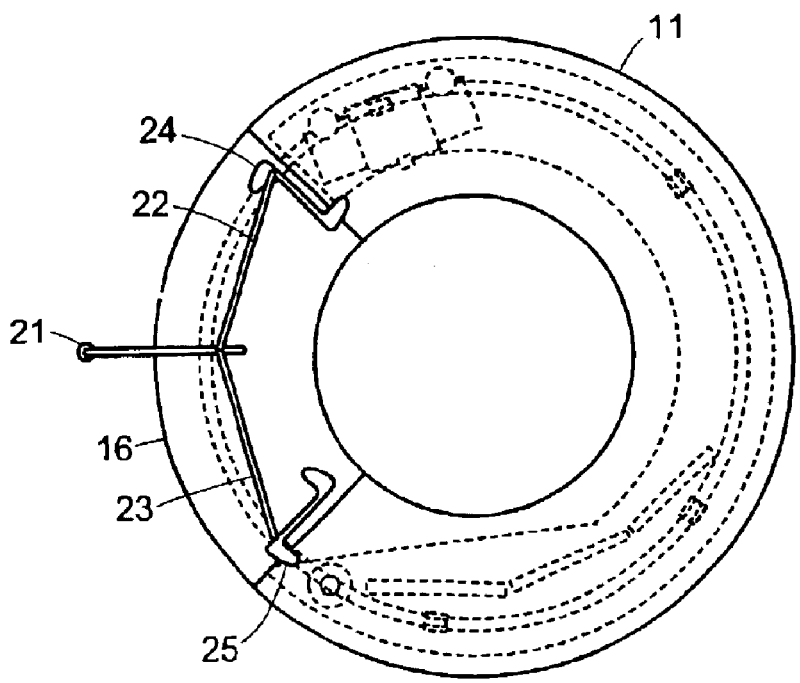
FIG. 10 shows the gantry ring of FIG. 8 with the gantry segment and latching mechanism in a closed and locked position.

In FIGS. 8–10, for example, a latching assembly 18 is used to secure or lock the hinged gantry segment 16 in place when the gantry is closed (for instance, during an x-ray imaging process). In a locked state, the hinged segment 16 is not permitted to pivot out from the closed gantry ring, and the x-ray source 13 and detector 14 can rotate 360 degrees around the inside of the closed gantry ring. However, the latching assembly 18 can also be easily unlocked, which permits the hinged segment 16 to be swung open.

In FIG. 8, for instance, the latching mechanism 18, which includes handle 21, linking members 22, 23, and upper and lower latches 24, 25, is in an unlocked position, while the hinged gantry segment 16 is in a fully open position. In FIG. 9, the gantry segment 16 is now in a closed position, but the latching mechanism 18 is still unlocked. As shown in FIG. 10, the latching mechanism 18 is locked by pulling handle 21 down into a locked position. The latching mechanism 18 can be easily unlocked by pushing the handle up to an unlocked position, and the hinged gantry segment 16 can then swing open.

Figure 11:
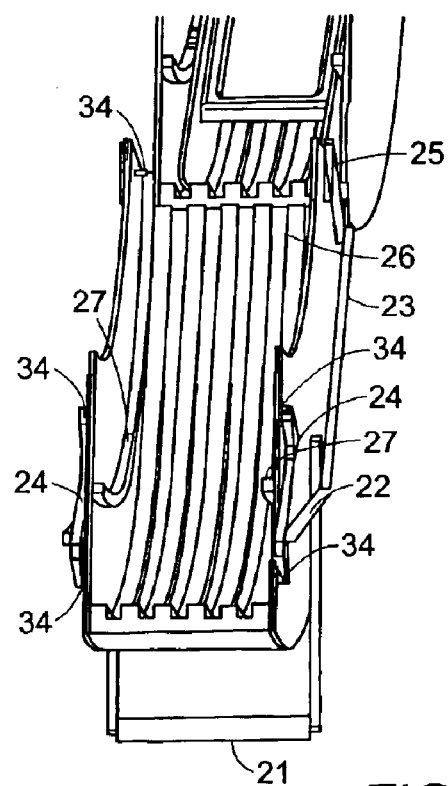
FIG. 11 shows the interior of a hinged gantry segment with rail and bearing assembly and latching mechanism.

In FIG. 11, the latching mechanism 18 is shown by way of an "end on" view of the interior of the open gantry segment 16. As shown here, spring-loaded alignment pins 34 on the hinged gantry segment 16 are driven into bushings 35 (see FIG. 8) on the fixed gantry 11 via a wedge-shaped latches 24, 25, causing the gantry segment 16 to be secured to the fixed gantry portion 11. The wedge-shaped latches 24,25 are driven by a linkage members 22, 23 connected to the handle 21 operated by a user. Also shown in this figure is a slip ring 26, which maintains electrical contact with the motorized rotor assembly 33 (see FIG. 12), and a curved rail 27, which guides the rotor assembly 33 as it rotates around the interior of the gantry 11, as will be described in further detail below. When the gantry is in a closed and locked position, the slip ring 26 and curved rail 27 of the detachable segment 16 align with the slip ring and curved rail of the fixed gantry, so that the motorized rotor assembly 30 (see FIG. 12) which carries the x-ray source and detector array can properly rotate within the gantry. During operation, the slip ring 26 preferably maintains electrical contact with the rotor assembly 30, and provides the power needed to operate the x-ray source/detector system, and to rotate the entire assembly within the gantry frame. The slip ring 26 can also be used to transmit x-ray imaging data from the detector to a separate processing unit located outside the gantry, such as in the mobile cart 12 of FIG. 1.

FIGS. 15A–E illustrate another embodiment of an x-ray imaging apparatus having a cable management system for rotating an x-ray source and detector array 360° around the interior of the gantry ring. In this example, the power for the x-ray source/detector system, as well as for rotating the x-ray source/detector within the gantry, is provided (at least in part) by a cable harness 36 containing one or more cables, in much the same manner as the slip ring described above. The cable harness 36 can also be used to transmit signals and data between the x-ray source/detector and an external processing unit.

Figure 15D:
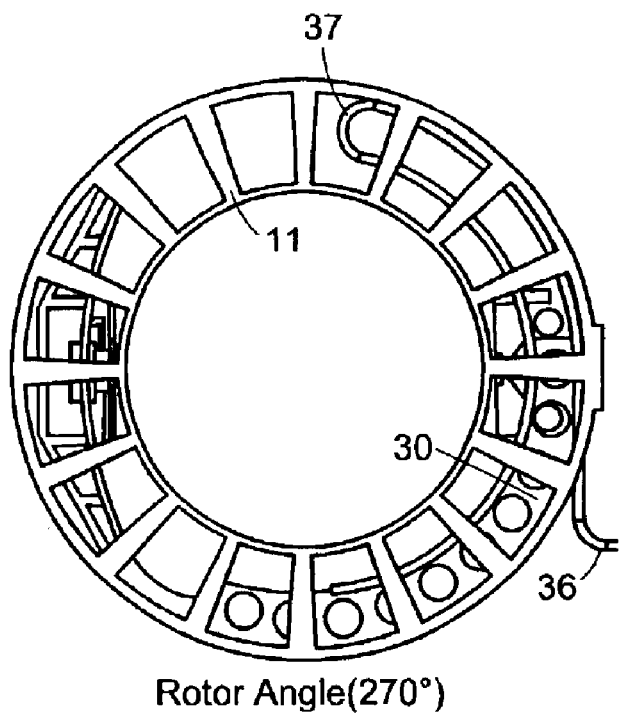
Figure 15E:
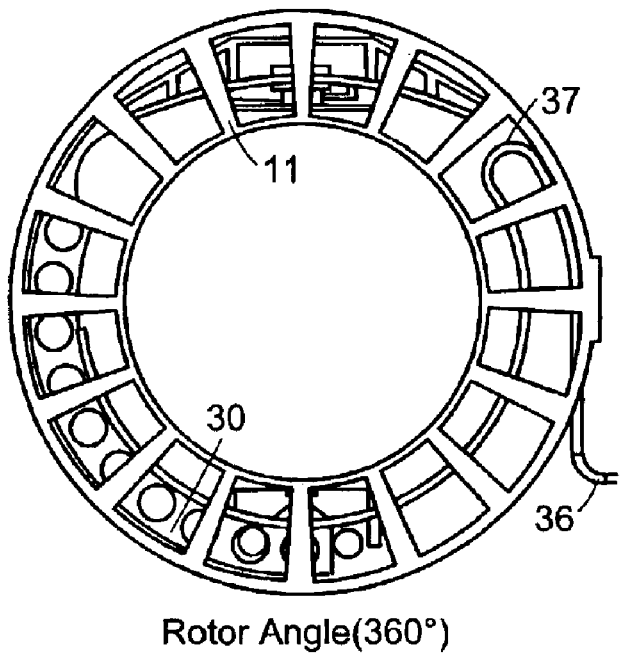

The cable harness 36 is preferably housed in a flexible, linked cable carrier 37. One end of the carrier 37 is fixed to a stationary object, such as the gantry 11 or the cart. The other end of the carrier 37 is attached to the motorized rotor assembly 33 which contains the x-ray source 13 and detector 14. In the example shown in FIGS. 15A–E, the rotor 33 starts at an initial position with the x-ray source 13 at the top of the gantry and the detector 14 at the bottom of the gantry (i.e. rotor angle=0°) as shown in FIG. 15A. The rotor 33 then rotates in a clockwise direction around the interior of the gantry, as illustrated in FIG. 15B (90° rotation), FIG. 15C (180° rotation), FIG. 15D (270° rotation), and FIG. 15E (360° rotation). In FIG. 15E, the rotor 33 has made a full 360° rotation around the interior of the gantry 11, and the rotor is again at the initial position with the x-ray source 13 at the top of the gantry, and the detector 14 at the bottom of the gantry. During the rotation, the cable carrier 37 remains connected to both the rotor 33 and gantry 11, and has sufficient length and flexibility to permit the rotor 33 to easily rotate at least 360° from the start position. To perform another 360° rotation, the rotor 33 can rotate counterclockwise from the end position of the prior rotation (e.g. rotor angle=360° in FIG. 15E) until the rotor 33 returns to the initial position of FIG. 15A. For continuous rotation, this process can repeat itself indefinitely with the rotor making full 360° rotations in alternatively clockwise and counterclockwise directions.

Figure 12:
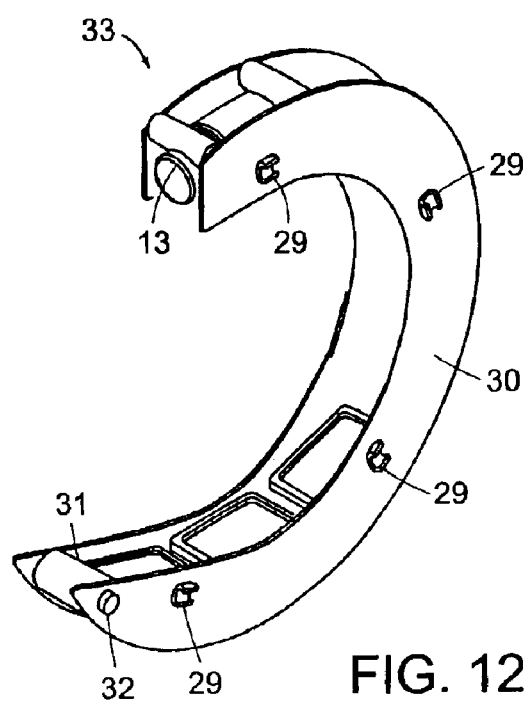
FIG. 12 illustrates a motorized rotor assembly for rotating an x-ray source and detector array within the gantry ring of an x-ray scanning device of the invention.

FIGS. 11 and 12 show one example of a rail and bearing mechanism for rotating the x-ray source 13 and detector 14 inside the gantry for performing two-dimensional and/or three-dimensional x-ray imaging procedures. As shown in FIG. 12, a motorized rotor assembly 33 includes the x-ray source 13 and the detector array 14 held within a rigid frame 30 designed to maintain a constant spacing between the source and detector as the rotor assembly rotates inside the x-ray gantry. (Note that the motorized rotor is generally c-shaped, with an open region at least as large as the detachable segment 16 of the gantry frame, so that the rotor assembly does not obstruct the opening of the gantry.) The rotor assembly 30 also includes a motor 31 and gear 32 for driving the rotor assembly around the interior of the gantry. As shown in FIG. 11, the interior side walls of the gantry include curved rails 27 which extend in a continuous loop around the interior of the gantry when the gantry is in a closed position. The gear 32 of the rotor assembly 30 contacts the curved rail 27 of the gantry, and uses the rail to drive the rotor assembly around the interior of the gantry. The rotor assembly 30 also includes curve rail carriages 29, which mate with the curved rails 27 of the gantry to help guide the rotor assembly 30 as it rotates inside the gantry.

The detector array 14 shown in FIG. 12 comprises three two-dimensional flat panel solid-state detectors arranged side-by-side, and angled to approximate the curvature of the gantry ring. It will be understood, however, that various detectors and detector arrays can be used in this invention, including any detector configurations used in typical diagnostic fan-beam or cone-beam CT scanners. A preferred detector is a two-dimensional thin-film transistor x-ray detector using scintillator amorphous-silicon technology.

For large field-of-view imaging, a detector 14 can be translated to, and acquire imaging data at, two or more positions along a line or arc opposite the x-ray source 13, such as via a motorized detector rail and bearing system. Examples of such detector systems are described in commonly owned U.S. Provisional Application 60/366,062, filed Mar. 19, 2002, the entire teachings of which are incorporated herein by reference.

Figure 13A:
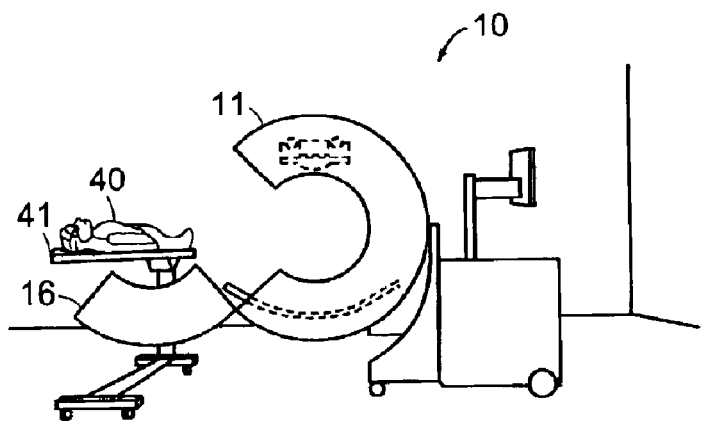
FIGS. 13A–C are schematic illustrations of a patient entering an x-ray scanning device through an open hinged segment of the gantry ring and the patient inside the closed gantry ring.
Figure 13B:
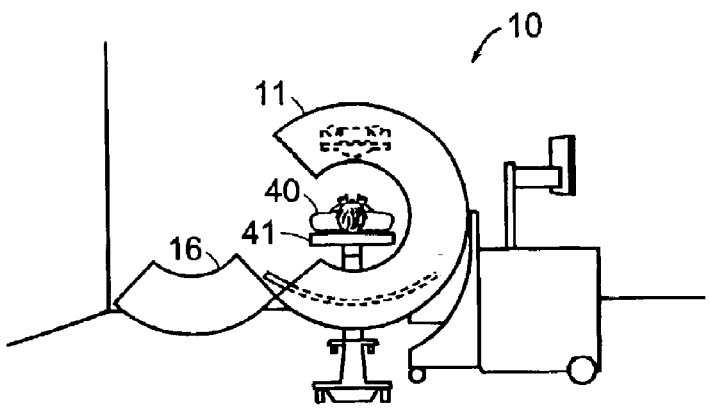
Figure 13C:
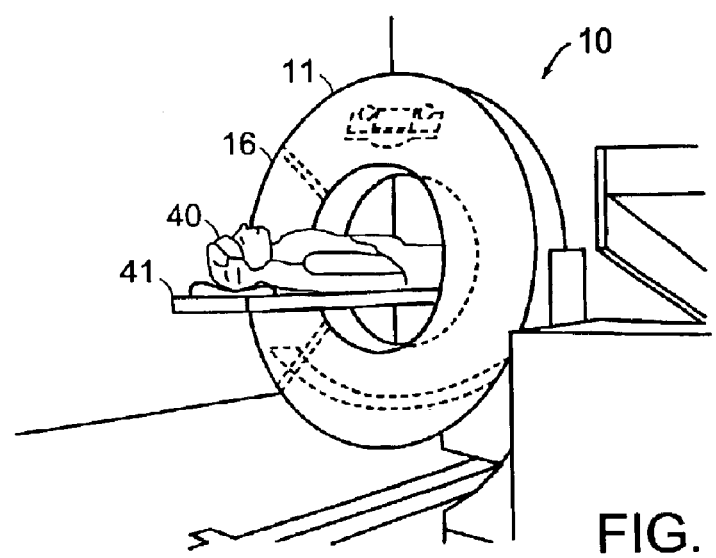

FIGS. 13A, B, and C show an embodiment of the scanner assembly 10 which is used for a medical imaging procedure. FIG. 13A, shows a patient 40 lying on a table 41 next to a mobile x-ray imaging apparatus 10 with a hinged segment 16 of the gantry ring 11 is fully open. The entire apparatus can then be moved in a lateral direction towards the patient (alternatively, or in addition, the patient can be moved towards the imaging apparatus), so that a region of interest of the patient is aligned within the x-ray gantry 11, as shown in FIG. 13B. Finally, as shown in FIG. 13C, the hinged segment 16 of the gantry 11 is closed, fully enclosing the patient within the gantry ring, and an x-ray imaging procedure is performed.

Figure 14:
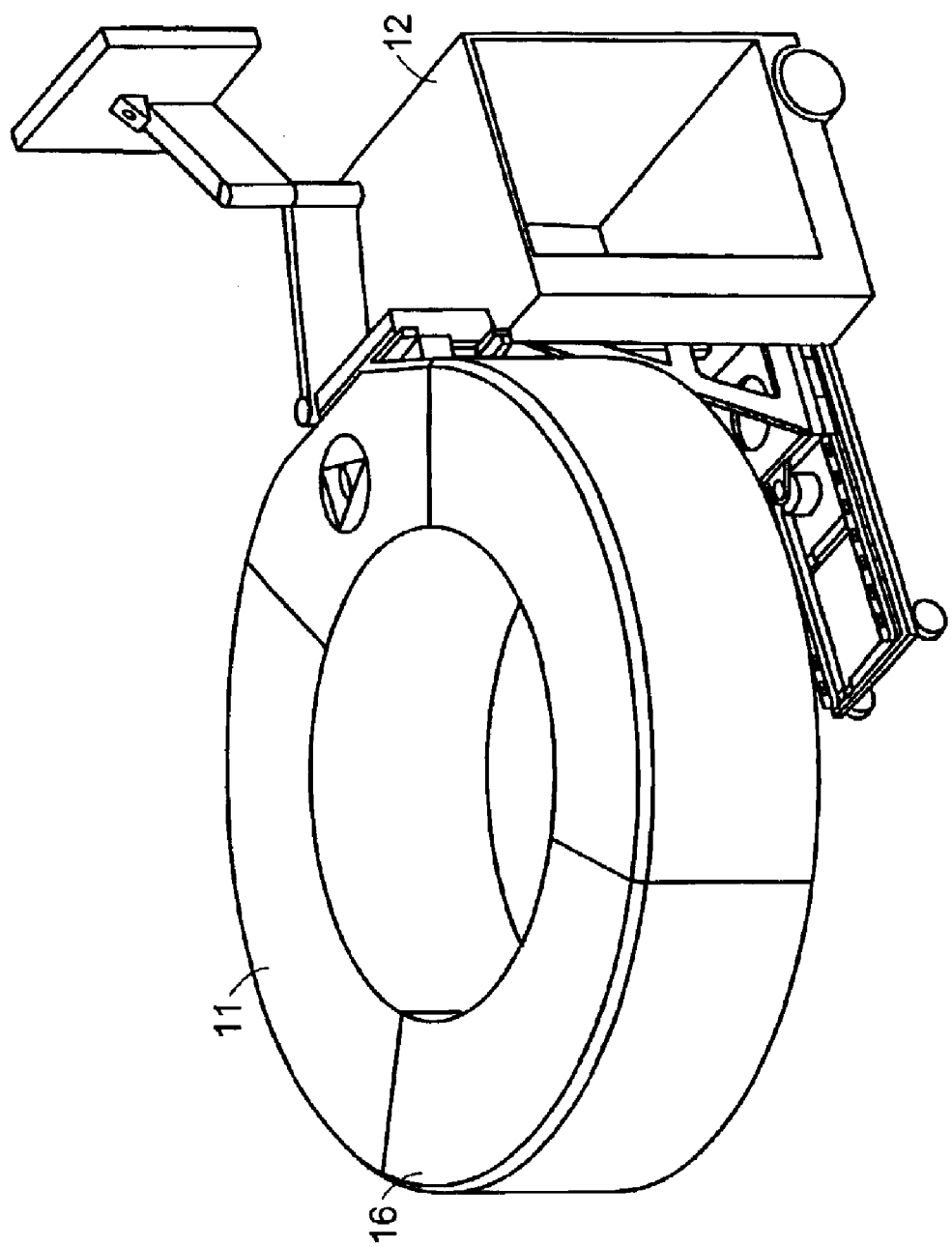
FIG. 14 illustrates an x-ray imaging apparatus having a vertical-axis gantry with a detachable gantry segment for imaging a standing or sitting patient.

In the embodiments shown and described thus far, the central axis of the gantry is oriented essentially horizontally, so that an object being imaged, such as a patient, lies lengthwise in the imaging area. In other embodiments, however, the gantry may be aligned so that its central axis extends at virtually any angle relative to the patient or object being imaged. For instance, the central axis of the gantry can be aligned essentially vertically, as shown in FIG. 14. Here, the central opening of the gantry is concentric with the "cylinder" formed by the torso of a standing or sitting human. As in the previous embodiments, the gantry includes a segment 16 that at least partially detaches from the gantry ring 11 to provide an opening or "break" in the gantry ring through which the object to be imaged may enter and exit the central imaging area of the gantry ring in a radial direction. The patient can enter the gantry via this opening in a standing or sitting position, and the segment can be easily re-attached for an imaging procedure. The entire imaging procedure can thus be performed while the patient remains in a standing or sitting position. Also, in addition to the medical procedures described, the vertical axis gantry may be useful for imaging other objects in which it is convenient to image the object while it is aligned in a standing or vertical orientation.

The x-ray imaging apparatus described herein may be advantageously used for two-dimensional and/or three-dimensional x-ray scanning. Individual two-dimensional projections from set angles along the gantry rotation can be viewed, or multiple projections collected throughout a partial or full rotation may be reconstructed using cone or fan beam tomographic reconstruction techniques.

While this invention has been particularly shown and described with references to preferred embodiments thereof, it will be understood by those skilled in the art that various changes in form and details may be made therein without departing from the scope of the invention encompassed by the appended claims.

For instance, although the particular embodiments shown and described herein relate in general to computed tomography (CT) x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.

Also, while the embodiments shown and described here relate in general to medical imaging, it will be understood that the invention may be used for numerous other applications, including industrial applications, such as testing and analysis of materials, inspection of containers, and imaging of large objects.

What is claimed is:

1. An imaging apparatus, comprising:
   a substantially O-shaped gantry ring having a central opening for positioning around an object to be imaged, the gantry ring having an interior cavity extending 360 degrees around the interior of the gantry ring;
   a detachable segment of the gantry that provides an opening in the gantry ring through which an object to be imaged may enter and exit the ring in a radical direction;
   a rigid C-shaped rotor housed within, and rotatable 360 degrees around, the interior cavity of the gantry ring;
   a drive mechanism secured to the rotor, and adapted to rotate the rotor around the interior of the gantry ring;
   a source of radiation secured to the rotor at a first position, the source adapted to project radiation onto said object as the source rotates 360 degrees around the interior of the gantry ring; and
   a detector secured to rotor at a second position, opposite the source on the gantry ring, positioned to detect the projected radiation.

2. The gantry apparatus of claim 1, further comprising a latching mechanism for attaching and detaching the gantry segment.

3. The gantry apparatus of claim 1, wherein the gantry segment is fully detachable from the gantry ring.

4. The gantry apparatus of claim 1, wherein the gantry segment is attached to the gantry ring via a hinge.

5. The gantry apparatus of claim 1, wherein the gantry segment telescopes with the gantry ring to provide the opening.

6. The gantry apparatus of claim 1, wherein the source is an x-ray source.

7. The gantry apparatus of claim 1, wherein the drive mechanism comprises a motor for rotating the rotor around the interior of the gantry.

8. The gantry apparatus of claim 7, wherein the motor is coupled to an external power source.

9. The gantry apparatus of claim 8, wherein the motor is coupled to an external power source via a slip ring.

10. The gantry apparatus of claim 8, wherein the motor is coupled to an external power source via a cable.

11. The gantry apparatus of claim 1, further comprising a bearing system for guiding the rotation of the rotor around the interior of the gantry.

12. The gantry apparatus of claim 1, wherein the detector rotates around the interior of the gantry in coordination with the rotation of the source.

13. The gantry apparatus of claim 1, wherein the gantry is secured to a mobile support structure.

14. The gantry apparatus of claim 13, wherein the mobile support structure comprises a cart.

15. The gantry apparatus of claim 1, wherein the gantry is secured to a support structure in a cantilevered fashion.

16. The gantry apparatus of claim 1, wherein the gantry can be translated along or rotated around at least one axis, and wherein the rotation of the rotor is independent of the movement of the gantry.

17. The gantry apparatus of claim 1, wherein the rotation of the rotor is independent of any movement of the gantry.

18. The gantry apparatus of claim 1, further comprising a processor which receives detected radiation data from the detector, and processes the data to produce an image of the object.

19. The gantry apparatus of claim 18, wherein the processor uses computerized tomography to produce a three-dimensional reconstructed image of the object.

20. The gantry apparatus of claim 1, wherein the object to be imaged comprises a human patient.

21. A method of imaging an object using radiation, comprising:
    positioning the object within a substantially O-shaped gantry ring via a radial opening in the gantry ring; and
    rotating a rigid C-shaped rotor 360 degrees around an interior cavity of the gantry ring, the rotor having a radiation source and detector mounted to the rotor, to image the object.

22. The method of claim 21, further comprising at least partially detaching a segment of the gantry ring to provide the radial opening.

23. The method of claim 21, further comprising attaching a segment of the gantry ring to close the radial opening.

24. The method of claim 21, wherein positioning the object comprises at least one of moving the object towards the gantry ring and moving the gantry ring towards the object.

25. The method of claim 21, further comprising:
    projecting radiation from the radiation source onto the object.

26. The method of claim 25, wherein the radiation comprises x-ray radiation.

27. The method of claim 21, further comprising:
    detecting radiation from the object.

28. The method of claim 27, further comprising:
    processing data corresponding to the detected radiation to produce an image of the object.

29. The method of claim 28, wherein the data is processed using computerized tomography to produce a three-dimensional reconstructed image of the object.

30. The method of claim 21, wherein the object being imaged comprises a human patient.

31. The method of claim 21, further comprising moving the gantry along or around an axis, where the movement of the gantry is independent of the rotation of the source and/or the detector.

* * * * *

UNITED STATES PATENT AND TRADEMARK OFFICE
CERTIFICATE OF CORRECTION

| | | |
|---|---|---|
| PATENT NO. | : 6,940,941 B2 | Page 1 of 1 |
| DATED | : September 6, 2005 | |
| INVENTOR(S) | : Eugene A. Gregerson et al. | |

It is certified that error appears in the above-identified patent and that said Letters Patent is hereby corrected as shown below:

Column 8,
Line 31, delete "radical" and insert -- radial --.

Signed and Sealed this

Twenty-ninth Day of November, 2005

JON W. DUDAS
*Director of the United States Patent and Trademark Office*